United States Patent [19]  
Bofinger et al.

[11] 4,319,577  
[45] Mar. 16, 1982

[54] SKULL TREPANATION DRILL

[75] Inventors: Gerhard Bofinger, Immendingen-Hattingen; Wilfried Wölfle, Bad-Dürrheim, both of Fed. Rep. of Germany

[73] Assignee: Aesculap-Werke Aktiengesellschaft, Tuttlingen, Fed. Rep. of Germany

[21] Appl. No.: 141,635

[22] Filed: Apr. 18, 1980

[30] Foreign Application Priority Data

Apr. 21, 1979 [DE] Fed. Rep. of Germany ....... 2916221

[51] Int. Cl.³ .............................................. A61B 17/32
[52] U.S. Cl. ................. 128/305.1; 279/1 B; 408/224
[58] Field of Search ............ 128/305.1, 310, 92 E; 408/239 R, 239 A, 224, 703; 279/75, 1 B, 2 R, 81

[56] References Cited

U.S. PATENT DOCUMENTS 2,525,669 10/1950 Hainault ............................. 128/310  
2,842,131 7/1958 Smith ................................. 128/310  
3,115,798 12/1963 Donaway ........................... 279/2 X

FOREIGN PATENT DOCUMENTS 950126 9/1949 France ............................... 128/310  
1094174 5/1955 France ............................ 128/305.1  
4440 of 1912 United Kingdom .............. 279/75  
1178275 1/1970 United Kingdom ............. 128/310

OTHER PUBLICATIONS

Leaflet of 3M Deutschland GmbH entitled "DAS Craniotome 30–ein 3M Produkt."

Primary Examiner—Michael H. Thaler  
Attorney, Agent, or Firm—Kenway & Jenney

[57] ABSTRACT

A skull trepanation drill having a drive shaft, a main cutter engageable with the drive shaft under axial force and a sleeve-shaped housing slidable axially and rotatably on the drive shaft and provided at its free end with an auxiliary cutter. In use, the sleeve-shaped housing is restrained from axial movement on the drive shaft by a locking body extending into recesses in the housing and drive shaft. The housing is manually releasable from the drive shaft for cleaning by rotation of a cam on the latter. The cam moves a lock bolt axially of the drive shaft to a position permitting the locking body to retract from the recess in the housing.

14 Claims, 3 Drawing Figures

SKULL TREPANATION DRILL

BACKGROUND OF THE INVENTION

The invention concerns a skull trepanation drill (bone drill) with a drive shaft connectable to a drive mechanism, with a sleeve-shaped housing surrounding the drive shaft and rotatably mounted on the latter, provided at its free end with a ring-shaped auxiliary cutter, with a main cutter mounted as an extension of the drive shaft in the interior of the housing in an axially displaceable manner, protruding beyond the auxiliary cutter, which can be connected in a rotationally rigid manner with the housing by means of a coupling element protruding beyond its circumference and engaging a recess on the inside of the housing, with a spring which forces the main cutter in the axial direction away from the drive shaft, with coupling elements on the end surface of the drive shaft and the opposing end surface of the main cutter for the purpose of rotationally coupling the main cutter and the drive shaft by mutual engagement when the main cutter is forced in the axial direction against the drive shaft, with at least one locking body mounted in the wall of the drive shaft and free to slide in the radial direction, which is forced into a first position by means of a locking bolt which is axially displaceable inside the hollow drive shaft and has at least one recess in its circumference and which protrudes beyond the circumference in its first position, thereby engaging into a recess on the inside of the sleeve-shaped housing, thereby securing the housing against axial displacement along the drive shaft, and which can be slid into a second position in which the recess in its circumference receives the locking body in such a manner that it no longer protrudes beyound the circumference of the drive shaft and thereby permits axial displacement of the housing on the drive shaft, and with a spring which slides the locking bolt into the first position.

Skull trepanation drills of this design have been exceptionally successful as so-called automatic skull trepanation drills, since the cutters are automatically decoupled from the drive shaft after completion of the skull boring, thereby preventing the danger of damage to the brain mass below the drilled skull bone. Skull trepanation drills of this type comprise a number of individual parts, and it is necessary to dis-assemble these individual parts completely for purposes of cleaning.

For this purpose the locking mechanism described above was found very suitable, in which the housing carrying the auxiliary cutter mounted on the drive shaft is secured to the drive shaft in the axial direction by a locking mechanism which comprises at least one locking body engaging a recess on the inside of the housing and free to slide in the radial direction in the outer wall of the drive shaft. To effect the radial displacement of the locking body there is provided in the hollow interior of the drive shaft, in one previously known skull trepanation drill, an axially displaceable locking bolt, which is held by means of a compression spring in a position in which locking bodies bear against its circumference and thereby protrude beyond the circumference of the drive shaft and engage into a recess on the inside of the housing. The locking bolt can be displaced against the action of the spring in the axial direction in such a manner that the locking bodies in the wall of the drive shaft are free to enter a recess in the circumference of the locking bolt, so that the locking bodies liberate the housing and permit its axial motion along the drive shaft.

In previously known skull trepanation drills of this design the displacement of the locking bolt inside the hollow drive shaft was achieved by displacing the locking bolt against the action of the spring by means of a pin through a concentric hole in the drive shaft. This design has not been found expedient in practice because it requires a separate tool. This involves the danger, particulary during assembly of the drill, that the sterile parts of the drill will be contaminated by this tool. Moreover, the proper tool must be available at the required instant, and this may also lead to problems in practice.

It is the object of the present invention to improve a skull trepanation drill of the type described above in such a manner that locking and unlocking of the individual parts is possible without the use of a separate tool. According to the invention, this task is solved in a skull trepanation drill of the design described above in that for axial displacement of the locking bolt the latter contacts a follower which slides in the drive shaft in the axial direction and by means of a cam surface which is secured against axial displacement along the drive shaft but is free to rotate about the longitudinal axis of the drive shaft, so that the follower bears against the cam surface and is displaced in the axial direction when the cam surface is rotated.

This design makes it possible in the simplest manner, by rotating the cam surface with respect to the drive shaft, to retract or extend the locking bodies in the drive shaft without the need for a separate tool.

It is expedient if the follower comprises a pin passing diametrically through the drive shaft and guided by two elongated holes in the wall of the drive shaft which are oriented parallel to its axis.

In the preferred embodiment of the invention it is provided that the cam surface bears in the axial direction under the pressure of the spring which slides the locking bolt against a stop attached to the drive shaft, which preferably comprises a ring flange.

It is also expedient if both the drive shaft and the cam surface are provided with a knurled flange so as to facilitate the relative displacement of the cam surface with respect to the drive shaft.

Additional expedient configurations of the invention constitute objects of the sub-claims.

DRAWINGS

The following description of a preferred embodiment of the invention serves for a more detailed explanation in connection with the drawing, which shows the following:

FIG. 1 a longitudinal section of a skull trepanation drill according to the invention;

FIG. 2 a partial side view of a skull trepanation drill according to the invention in the region of the cam surface, and FIG. 3 a sectional view along the lines 3—3 in FIG. 1.

DETAILED DESCRIPTION

Figure 1:
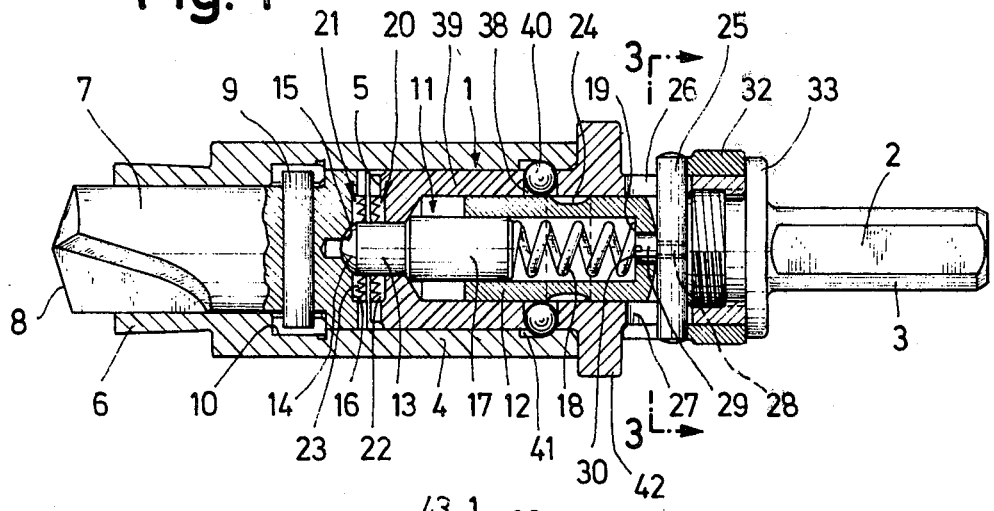

The skull trepanation drill represented in the drawing comprises a hollow drive shaft 1, provided with a connecting tang 3 with flattened surfaces 2 for connecting it in a rotationally rigid manner to a drive mechanism not shown in the drawing. Over the free end of the drive shaft 1 there is slipped a sleeve-shaped housing 4 which bears with its inner surface intimately against the circumference of the drive shaft 1, and protrudes beyond the free end surface 5 of drive shaft 1. On the free end of the sleeve-shaped housing 4 there is located a ring-shaped auxiliary cutter 6 which is either an integral part of housing 4, or is rigidly connected to it.

As an extension of the drive shaft 1, there is mounted inside the sleeve-shaped housing 4 a main cutter 7 which is guided by its body inside the ring-shaped auxiliary cutter 6 and whose cutting surfaces 8 protrude beyond the cutting surfaces of the auxiliary cutter 6. The main cutter 7 is free to slide in the axial direction in housing 4 and is traversed diametrically by a follower pin 9, which engages into corresponding grooves 10 in the inner wall of housing 4, so that the main cutter 7 on the one hand, and the housing 4 with the auxiliary cutter 6 on the other hand are connected in a rotationally rigid manner.

Inside the hollow drive shaft 1, there is located a spring bolt 11, which is free to slide in the axial direction inside a hollow locking bolt 12. The spring bolt 11 protrudes with an extension 13 through the end surface 5 of the drive shaft 1, and bears with its spherical end 14 into a cup-shaped depression 15 in the end surface 16 of the main cutter 7.

Against the opposite end 17 of the spring bolt 11 there bears a pressure spring 18 whose opposite end bears against the inside of the end surface 19 of a locking bolt 12, which will be described in further detail below. Thus the main cutter 7 is pushed away from the drive shaft 1 by means of the spring bolt 11.

The end surface 5 of drive shaft 1, and the end surface 16 of the main cutter 7 exhibit ring-shaped coupling elements 20 and 21 respectively with saw-tooth-shaped engaging elements 22 and 23. When the main cutter 7 is displaced in the axial direction against the action of the pressure spring 18, the coupling elements 20 and 21 are brought into engagement and connect the main cutter (and the auxiliary cutter which is connected to it through pin 9 and grooves 10) to the drive shaft in a rotationally rigid manner. As soon as the axial displacement of the main cutter 7 ceases, for example because the drill has passed through the skull bone and there is no longer any axial resistance, the main cutter will move away from the drive shaft so that the rotational connection is immediately broken.

The locking bolt 12, which is free to slide inside the drive shaft 1, has the shape of a sleeve closed at one end, into which a Circumferential groove 24 has been machined. The locking bolt is forced under action of the compression spring 18 against a follower 25 in the form of a pin passing transversely through the drive shaft and guided so that it is free to slide in axially elongated holes 26, 27 in the drive shaft. The follower 25 extends on both sides beyond the circumference of the drive shaft 1. It is secured against displacement in its longitudinal direction by the fact that a screw 28 is screwed into it in the radial direction, the head 29 of this screw engaging into a central aperture 30 in the end surface 19 of the locking bolt 12.

Figure 2:
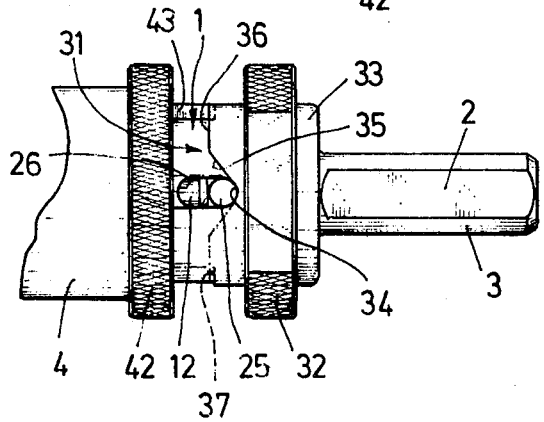
Figure 3:
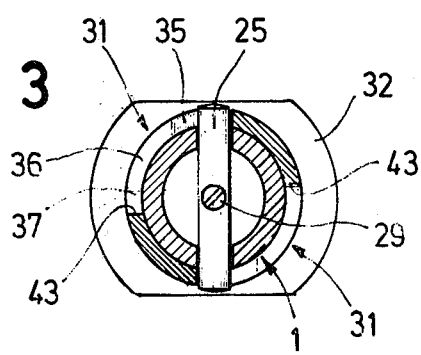

As best indicated in FIG. 2, there is mounted on drive shaft 1 a cam surface 31 which is free to rotate about the longitudinal axis of the drive shaft 1. The cam surface 31 is connected to a knurled flange 32 and bears against a ring-flange shaped stop 33 of drive shaft 1. The free ends of the pin-shaped follower 25 are pressed against the cam surface 31 under action of the compression spring 18.

The cam surface 31 exhibits different ranges 34, 35 and 36 (FIG. 2) against which the follower 25 bears in succession when the cam surface is rotated. When it bears in the range 34, the compression spring assumes its most relaxed position, when it bears in the range 36, the spring assumes its most compressed position. The Obliquely inclined range 35 [ramp] connects the ranges 34 and 36.

In the preferred embodiment, two oppositely located ranges 34 and two oppositely located ranges 36 are provided, which are displaced with respect to each other by 90 degrees. The ranges 36 exhibit a depression 37 in which the follower 25 can rest under action of the compression spring 18.

As indicated in FIG. 1, the radial orifices 38 in the wall 39 of drive shaft 1, in the present case, contain locking bodies 40 in the shape of spheres, which are free to slide in the radial direction but are secured from falling out of the drive shaft 1 in the radial direction. When these locking bodies bear against the outer circumference of the locking bolt 12, as represented in FIG. 1, they protrude beyond the circumference of drive shaft 1 and engage into recesses 41 on the inside of housing 4, so that this housing is secured against displacement.

When the locking bolt is displaced against the action of compression spring 18, the circumferential groove 24 arrives at the location of the recesses 38, so that the spherical locking bodies 40 are free to move radially inward, thereby liberating the housing 4 in the axial direction. In this position the skull trepanation drill can be disassembled into its individual parts.

Displacement of the locking bolt in the axial direction is accomplished in a simple manner in the design described by rotating the cam surface with respect to the drive shaft, for which purpose the drive shaft is provided with a knurled flange 42, protruding in the radial direction. When the follower bears against range 34, the housing is locked (normal position), when the follower bears against range 36 and particularly against the depression 37, the lock of housing 4 is open (open position). In this manner the lock can be opened very simply, without the use of any tools.

The cam surface may exhibit different shapes. The solid lines in FIG. 2 represent a shape in which the ranges 34 and 36 are each followed by ranges 43, which are parallel to the axis of the drive shaft and which serve, together with follower 25, as rotational stops for the cam surface. It is also possible, however, to design the cam surface in the shape of the broken line in FIG. 2, so that rotation from the normal position into the opened position and vise-versa can take place in both directions.

We claim:

1. In a skull trepanation drill of the class including a tubular drive shaft having a first recess in a wall thereof, a sleeve-shaped housing slidable axially and rotatably on the drive shaft and having a second recess in a wall thereof, a cutter rotatably fixed with respect to the housing and engageable for rotation by the drive shaft, a lock bolt slidable in the drive shaft and having a third recess in a wall thereof, a locking body located within and partially protruding from the first recess and being movable therein radially of the drive shaft, the lock bolt being slidable axially of the drive shaft between a locking position wherein it forces the locking body into the first and second recesses to restrain the housing from axial movement on the drive shaft, and a release position permitting the locking body to move into the third recess and out of the second recess, and spring means urging the lock bolt toward the locking position, the combination with said lock bolt of

- a follower axially slidable on the drive shaft and engaging the lock bolt, and
- a cam secured against axial displacement along the drive shaft, having a cam surface with a portion thereof bearing on the follower and being rotatable on the drive shaft to cause an annularly displaced portion of the cam surface to bear on the follower, thereby causing the follower to move axially of the drive shaft to move the lock bolt between said locking and release positions.

2. The combination according to claim 1, in which the drive shaft has a pair of diametrically opposed elongate holes in the wall thereof and the follower comprises a pin extending laterally of the drive shaft through said holes.

3. The combination according to claim 2, in which the lock bolt has a recess extending axially of the drive shaft and the pin has a protrusion extending into said last-mentioned recess.

4. The combination according to claim 3, in which the protrusion comprises a screw threaded into the pin transversely of its principal dimension.

5. The combination according to either of claim 1 or 2, in which the drive shaft has a radially extending stop and said spring means urges the lock bolt in a direction to cause the cam means to bear against said stop.

6. The combination according to claim 5, in which the stop is a ring flange.

7. The combination according to claim 5, in which the cam surface has a first range for locating the lock bolt in the locking position, the spring means being under less stress in the locking position than it is in the release position.

8. The combination according to claim 5, in which the cam surface has a second range with a depression therein for locating the lock bolt in the release position, the spring means being under greater stress in the release position than it is in the locking position.

9. The combination according to claim 5, in which the cam surface has a pair of diametrically opposed first ranges for locating the lock bolt in the locking position and a pair of diametrically opposed second ranges for locating the lock bolt in the release position.

10. The combination according to claim 9, in which the cam surface has an obliquely inclined ramp connecting first and second ranges.

11. The combination according to claim 5, in which the cam surface has first and second ranges for locating the lock bolt respectively in the locking and release positions, and a range oriented parallel to the axis of the drive shaft and rotatable to a position abutting the follower wherein the follower prevents further rotation of the cam.

12. The combination according to claim 1, in which the drive shaft and cam means each have knurled flanges adapted for manual rotational displacement therebetween.

13. The combination according to claim 1, in which the cutter is slidable within the housing, said spring means bearing on a spring bolt adapted to seat on the lock bolt with a portion thereof extending axially from the drive shaft into engagement with the cutter, the cutter and drive shaft having mutually engageable coupling elements, whereby an axial force on the cutter is required to overcome the force of the spring means through the spring bolt to permit engagement of said coupling elements.

14. The combination according to claim 1, in which the housing is provided at its free end with an auxiliary cutter.

* * * * *